US006924398B2

(12) United States Patent
Pan et al.

(10) Patent No.: US 6,924,398 B2
(45) Date of Patent: Aug. 2, 2005

(54) SUBSTITUTED TROPOLONE COMPOUNDS, ORAL CARE COMPOSITIONS CONTAINING THE SAME AND METHODS OF USING THE SAME

(75) Inventors: Pauline Pan, Denville, NJ (US); Marybeth Finnegan, Hillsborough, NJ (US); Andre Soshinsky, Randolph, NJ (US); Georgia Arvanitis, Ewing, NJ (US); Michael Berardini, Ewing, NJ (US)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 10/827,505

(22) Filed: Apr. 19, 2004

(65) Prior Publication Data

US 2004/0204501 A1 Oct. 14, 2004

Related U.S. Application Data

(63) Continuation of application No. 10/207,618, filed on Jul. 29, 2002, now Pat. No. 6,787,675.

(51) Int. Cl.$^7$ ............................................ C07C 49/105
(52) U.S. Cl. ............................................................ 568/375
(58) Field of Search ............................ 568/375; 514/546, 514/690; 424/49, 401

(56) References Cited

U.S. PATENT DOCUMENTS

| 4,152,457 A | * | 5/1979 | Bagli et al. ................. 424/305 |
| 4,656,192 A | * | 4/1987 | Yamato ....................... 514/564 |
| 4,950,686 A | * | 8/1990 | Kondo et al. ............... 514/546 |
| 5,009,898 A |   | 4/1991 | Sakuma et al. ............. 424/618 |
| 5,696,169 A |   | 12/1997 | Otsu et al. ................. 514/675 |
| 5,939,050 A |   | 8/1999 | Iyer et al. ..................... 424/49 |
| 6,025,312 A |   | 2/2000 | Saito et al. ................. 510/130 |
| 6,096,328 A |   | 8/2000 | Sagel et al. ................. 424/401 |
| 6,689,342 B1 | * | 2/2004 | Pan et al. ..................... 424/49 |

FOREIGN PATENT DOCUMENTS

| EP | 900560 | 3/1999 |
| JP | 47043218 | 12/1972 |
| JP | 51023244 | 2/1976 |
| JP | 51033901 | 9/1976 |
| JP | 53099339 | 8/1978 |
| JP | 59175410 | 10/1984 |
| JP | 60016913 | 1/1985 |
| JP | 60116631 | 6/1985 |
| JP | 61100516 | 5/1986 |
| JP | 61286314 | 12/1986 |
| JP | 62181212 | 8/1987 |
| JP | 63005048 | 1/1988 |
| JP | 63188619 | 4/1988 |
| JP | 01305021 | 12/1989 |
| JP | 02027991 | 1/1990 |
| JP | 02069411 | 3/1990 |
| JP | 03000789 | 1/1991 |
| JP | 03115213 | 5/1991 |
| JP | 03151317 | 6/1991 |
| JP | 03193743 | 8/1991 |
| JP | 03271215 | 12/1991 |
| JP | 03279321 | 12/1991 |
| JP | 04198121 | 7/1992 |
| JP | 47043218 | 8/1993 |
| JP | 07133214 | 5/1995 |
| JP | 07187973 | 7/1995 |
| JP | 07187977 | 7/1995 |
| JP | 07233397 | 9/1995 |
| JP | 07258050 | 10/1995 |
| JP | 08003074 | 1/1996 |
| JP | 08040971 | 2/1996 |
| JP | 08183997 | 7/1996 |
| JP | 08193056 | 7/1996 |
| JP | 09188620 | 7/1997 |
| JP | 09188892 | 7/1997 |
| JP | 10182383 | 7/1998 |
| JP | 10194943 | 7/1998 |
| JP | 10212220 | 8/1998 |
| JP | 63211217 | 9/1998 |
| JP | 63211218 | 9/1998 |
| JP | 11001465 | 1/1999 |
| JP | 11012142 | 1/1999 |
| JP | 11060550 | 3/1999 |
| JP | 11130648 | 5/1999 |
| JP | 1158051 | 6/1999 |
| JP | 11158052 | 6/1999 |
| JP | 11197217 | 7/1999 |
| JP | 11222455 | 8/1999 |
| JP | 11228379 | 8/1999 |
| JP | 11256191 | 9/1999 |
| JP | 20000044422 | 2/2000 |
| WO | WO 98/44901 | 10/1998 |
| WO | WO 2000/016736 | 3/2000 |

* cited by examiner

*Primary Examiner*—Johann Richter
*Assistant Examiner*—Sikarl A. Witherspoon
(74) *Attorney, Agent, or Firm*—Erika Singleton Wilson; Darryl C. Little

(57) ABSTRACT

The present invention relates to novel tropolone compounds of the present invention and to oral care compositions suitable for preventing or treating diseases or conditions of the oral cavity in warm-blooded animals including humans, comprising an oral care effective amount of at least one novel tropolone compounds, and a pharmaceutically acceptable oral carrier. This invention further relates to a method for preventing or treating diseases or conditions of the oral cavity in warm-blooded animals including humans, by applying an oral care effective amount of the oral care composition to the oral cavity.

8 Claims, No Drawings

SUBSTITUTED TROPOLONE COMPOUNDS, ORAL CARE COMPOSITIONS CONTAINING THE SAME AND METHODS OF USING THE SAME

PRIORITY INFORMATION

This continuation application of U.S. patent application Ser. No. 10/207,618, filed on Jul. 29, 2002 now U.S. Pat. No. 6,787,675, the entirety of which is hereby incorporated by reference as if fully set forth herein.

FIELD OF THE INVENTION

The present invention is related generally to tropolone compounds, more particularly to substituted tropolone compounds and compositions containing the same, and methods of using the same for oral care.

BACKGROUND OF THE INVENTION

Oral malodor, plaque, gingivitis, periodontal disease, and discoloration of the teeth, are all undesirable conditions that affect many people. First malodor of the oral cavity also known as halitosis or oral malodor has been broadly estimated to afflict 20 to 90 million individuals in the U.S. It is generally believed that the presence of anaerobic bacteria, especially gram-negative anaerobic bacteria, in the mouth contributes to this condition. Other oral conditions caused by microorganisms include periodontal disease, tooth decay, inflammation and the like.

Periodontal disease is a major cause of tooth loss in adults, and can manifest itself in people as young as age 12. Periodontal disease affects the periodontum, which is the investing and supporting tissues surrounding a tooth (i.e., the periodontal ligament, the gingiva, and the alveolar bone). Gingivitis and periodontatitis are disorders of the gingiva and the deeper periodontal tissues, respectively. Periodontal disease is generally associated with the accumulation of plaque on the teeth. The teeth are coated with a salivary proteinaceous material (pellicle) and thereafter streptococci adhere to this coating. Gingivitis occurs from the dental plaque, and periodontatitis is caused by the infection spreading to the periodontal pocket or space between the gingival and the tooth root.

Many of the current oral care compositions including toothpastes, mouthwashes, rinses and tooth gels are formulated to clean the oral cavity and kill pathogenic microbes. Such oral care compositions are typically formulated with one or more antimicrobial agents to suppress microorganisms that contribute both to the initiation and progression of oral malodor, periodontal disease and other undesirable oral conditions. One such antimicrobial agent is hinokitiol, or beta-thujaplicin. Hinokitiol has been used as an antiseptic that exhibits low stimulative or irritative effects on the skin of the human body. However, hinokitiol is not very water-soluble, and is not sufficiently stable under all conditions in which its use is desirable. Compositions containing hinokitiol lose antimicrobial efficacy when exposed to air and light, and form hinokitiol precipitates on the walls of the container, thus further reducing the efficacy and usefulness of such compositions.

There is a need for developing efficacious oral care compositions such as mouthwashes or rinses, containing antimicrobial agents having favorable antimicrobial kinetics while exhibiting suitable chemical stability and solubility for effective delivery of the agents to the oral cavity. There is a need for compositions with enhanced antimicrobial kinetics to provide effective prevention or treatment of diseases and conditions of the oral cavity by killing pathogenic oral microorganisms responsible for plaque, gingivitis and other undesirable oral conditions.

SUMMARY OF THE INVENTION

There are provided novel compounds having antimicrobial properties that are especially effective for use in oral care products. In accordance with the present invention, tropolone compounds exhibiting such properties are disclosed. In one aspect of the present invention, there are provided compounds of Formula (I), isomers and pharmaceutically acceptable salts thereof,

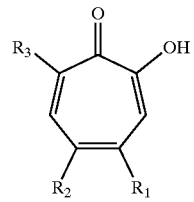

I wherein $R_1$, $R_2$, and $R_3$ are each independently selected from the group consisting of hydrogen, an alkyl group, a hydroxyalkyl group, and an alkoxyalkyl group, with the proviso that when $R_2$ and $R_3$ are each hydrogen, then $R_1$ is not isopropyl.

In a preferred embodiment, $R_1$, $R_2$, and $R_3$ are each independently selected from the group consisting of hydrogen, an alkyl group having 1 to 6 carbon atoms, a hydroxyalkyl group having 1 to 6 carbon atoms, and an alkoxyalkyl group wherein the "alkoxy" portion and the "alkyl" portion each have from 1 to 6 carbon atoms.

In another aspect of the present invention, there is provided an oral care composition for preventing or treating diseases and conditions of the oral cavity, comprising an oral care effective amount of at least one of the compounds of Formula (I), and isomers and pharmaceutically acceptable salts thereof, and a pharmaceutically acceptable oral carrier.

In a further aspect of the present invention, there is provided a method for preventing or treating diseases and conditions of the oral cavity in warm-blooded animals including humans, comprising applying an oral care effective amount of the present oral care composition to the oral cavity.

DETAILED DESCRIPTION OF THE INVENTION

The present invention is directed to novel tropolone compounds exhibiting effective antimicrobial properties suitable for use in oral care products. The present invention is further directed to oral care compositions including dentifrice, mouthwash or rinse, oral gel, lozenge, mouth spray, and the like, that comprise the novel tropolone compounds effective for cleaning the oral cavity and/or preventing or treating diseases or conditions of the oral cavity in warm-blooded animals including humans, including, but not limited to, gingivitis, periodontatitis, oral malodor, tooth decay and the like. The oral care compositions of the present invention provide a high degree of antiseptic efficacy against microorganisms, and particularly oral microorganisms, including, but not limited to, *Fusobacterium nucleatum, Prevotella intermedia, Actinomyces viscosus, Campylobacter rectus, Porphyromonas gingivalis, Streptococcus sanguis, Streptococcus mutans, Actinobacillus, Bacteroides,*

*Capnocytophaga, Eikenella, Propionibacterium,* and *Candida albicans* responsible for oral malodor and build-up of plaque and calculus and the resulting tooth and gum diseases that may follow.

The present invention is also directed to methods of cleaning the oral cavity, and/or preventing or treating diseases or conditions of the oral cavity in warm-blooded animals including humans, by applying to the oral cavity, an oral care effective amount of the oral care composition containing the tropolone compounds of the present invention.

In one embodiment of the present invention, there are provided compounds of Formula (I), and isomers and pharmaceutically acceptable salts thereof,

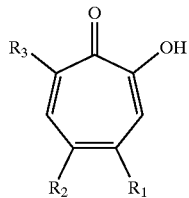

I wherein $R_1$, $R_2$, and $R_3$ are each independently selected from the group consisting of hydrogen, an alkyl group, a hydroxyalkyl group, and an alkoxyalkyl group, with the proviso that when $R_2$ and $R_3$ are each hydrogen, then $R_1$ is not isopropyl.

The term "alkyl", "hydroxyalkyl", and "alkoxyalkyl" cover all such groups exhibiting the desired oral activity. Preferably each of said groups has from about 1 to 6 atoms (i.e., the alkyl portion of the group has 1 to 6 carbon atoms and the alkoxy portion of the group has 1 to 6 carbon atoms).

The term "pharmaceutically acceptable salt" refers to pharmaceutically acceptable salts which are derived from a variety of organic and inorganic cations well known in the art and include, by way of example only, sodium, potassium, calcium, magnesium, ammonium, tetraalkylammonium, and the like, and anions, such as hydrochloride, hydrobromide, tartrate, mesylate, acetate, maleate, oxalate, and the like.

Isomers of the compounds of Formula (I) having the desired antimicrobial activity mixtures thereof are included in the scope of the present invention.

In addition, hydrates and solvates with pharmaceutically acceptable organic solvents, as well as prodrugs of the compounds of the present invention are also encompassed by the present invention.

In addition, compounds of Formula (I) or pharmaceutically acceptable salts thereof may be present in the form of addition products with water or various solvents, and these addition products are also included in the scope of the present invention.

The term "pharmaceutically acceptable salts" refers to salts prepared from pharmaceutically acceptable non-toxic bases or acids including inorganic or organic bases and inorganic or organic acids. They can be derived from a variety of organic and inorganic cations well known in the art and include, by way of example, sodium, potassium, calcium, magnesium, ammonium, tetraalkylammonium, and the like, and anions, such as hydrochloride, hydrobromide, tartrate, mesylate, acetate, maleate, oxalate, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids. Salts derived from inorganic bases include aluminum, ammonium, calcium, copper, ferric, ferrous, lithium, magnesium, manganic salts, manganous, potassium, sodium, zinc, and the like.

Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Those skilled in the art will recognize a wide variety of non-toxic pharmaceutically acceptable addition salts.

The compounds of Formula (I), and isomers and pharmaceutically acceptable salts thereof may also be collectively referred to as "tropolone compounds of the present invention."

In one preferred embodiment, the tropolone compounds of the present invention are selected from the group consisting of 4-methyl-7-hydroxymethyltropolone, 4,7-dimethyltropolone, 4-methyl-7-methoxymethyltropolone, 4-isopropyl-7-methyltropolone, 4-isopropyl-7-hexyltropolone, 4-t-butyltropolone, 5-t-butyltropolone, 4-methyltropolone, 4-isopropyl-7-methoxymethyltropolone, 4-isopropyl-7-hexloxymethyltropolone, and combinations thereof.

In another embodiment of the present invention, there are provided oral compositions useful for oral care including preventing or treating diseases or conditions of the oral cavity in warm-blooded animals including humans, which comprise an oral care effective amount of at least one of the compounds of Formula (I) and isomers and pharmaceutically acceptable salts thereof, and a pharmaceutically acceptable oral carrier. The term "oral care composition" is meant to include products which are retained in the oral cavity for a sufficient time to contact the dental surfaces and/or oral mucosal tissues and exhibit the desired oral activity.

The term "diseases or conditions of the oral cavity," as used herein, is meant to include diseases of the oral cavity including, but not limited to, periodontal disease, gingivitis, periodontatitis, periodontosis, adult and juvenile periodontatitis, and other inflammatory conditions of the tissues within the oral cavity in warm-blooded animals including humans, plus caries, necrotizing ulcerative gingivitis, and other conditions such as oral malodor. The compositions and methods of treatment and oral care of the present invention are particularly effective for preventing or treating periodontal disease (gingivitis and/or periodontatitis) and oral malodor in warm-blooded animals including humans.

Oral care compositions, which are preferred, may be selected, for example, from the group consisting of mouthwash or rinse, toothpaste, tooth powder, dental cream, dental floss, liquids, gels, chewing gum, liquid center filled gums, mints, lozenges, oral film forming dentifrices, and the like.

The oral care compositions of the present invention comprise a pharmaceutically acceptable oral carrier, in an amount appropriate to accommodate the other components of the formulation. The term "pharmaceutically acceptable oral carrier" refers to a vehicle capable of being mixed with the active components for delivery to the intended target in an oral cavity, and which will not cause unacceptable harm to warm-blooded animals including humans. The oral carriers further include those components of the composition that are capable of being commingled without interaction in a manner which would substantially reduce the composition's stability and/or efficacy for oral care including preventing or treating diseases or conditions of the oral cavity in warm-blooded animals including humans, in accordance with the compositions and methods of the present invention.

The pharmaceutically acceptable oral carriers of the oral care compositions can include one or more compatible solid or liquid filler diluents or encapasulating substances, which are suitable for oral administration. The carriers or excipients of the present invention may be in any form appropriate to the mode of delivery, for example, solutions, colloidal dispersions, emulsions, suspensions, rinses, gels, foams, powders, solids, and the like, and can include the usual and conventional components of toothpastes (including gels and gels for subgingival application), mouthwashes and rinses, mouth sprays, chewing gums, and lozenges (including breath mints). Carriers suitable for the preparation of compositions of the present invention are well known in the art. Their selection will depend on secondary considerations like taste, cost, and shelf stability, etc.

Types of carriers which may be included in the oral compositions of the present invention are abrasives, fluoride ions, thickening agents, humectants, flavoring and sweetening agents, anticalculus agents, alkali metal bicarbonate salts, surfactants including nonionic, amphoteric surfactants, and anionic surfactants, and miscellaneous carriers such as water, as well as titanium dioxide, anti-inflammatory agents, and the like.

Preferred compositions of the present invention are mouthwashes, rinses, and mouth sprays. Components of such mouthwashes, rinses and mouth sprays typically include water in an amount from about 45% to 95% by weight based on the total weight of the oral care composition, and one or more of ethanol in an amount up to 30% by weight, a humectant in an amount up to 50% by weight, a surfactant in an amount of from about 0.01% to 7% by weight, a flavoring agent in an amount of from about 0.04% to 2% by weight, a sweetening agent in an amount of from about 0.1% to 3% by weight, and a coloring agent in an amount of from about 0.001% to 0.5% by weight. Such mouthwashes, rinses and mouth sprays may also include one or more of an anticaries agent from in an amount of about 0.05% to 0.3% by weight (e.g., fluoride ion), and an anticalculus agent in an amount of from about 0.1% to 3% by weight.

Other preferred compositions of the present invention are dental solutions. Components of such dental solutions generally include water in an amount of from about 90% to 99% by weight based on the total weight of the oral care composition, and one or more of a preservative in an amount of from about 0.01% to 0.5% by weight, a thickening agent in an amount up to 5% by weight, a flavoring agent in an amount of from about 0.1% to 3% by weight, and a surfactant in an amount up to 5% by weight.

Other preferred compositions of the present invention are consumable films or thin strips. Orally consumable films typically comprise a rapidly dissolvable non-self-adhering polymer-based thin film vehicle. Such compositions are typically administered to the oral cavity where they rapidly dissolve upon contact with saliva and provide rapid delivery of the active ingredients. LISTERINE® POCKETPAKS™ brand oral care strip products made by PFIZER, Inc. of Morris Plains, N.J. are perhaps the most successful examples of an edible film compositions effective in delivering therapeutic agents particularly antimicrobial agents in the form of LISTERINE® essential oils to the oral cavity. Components of such compositions generally include water in an amount up to 75% by weight based on the total weight of the oral care composition, a water soluble film forming polymer including, but not limited to, pullulan, in an amount of up to 25% by weight, a flavoring agent in an amount of from about 0.01% to 10% by weight, a surfactant in an amount up to 5% by weight, and optionally, copper salts in an amount of from about 0.01% to 5% by weight.

Other preferred compositions of the present invention are in the form of dentifrices such as toothpastes, tooth gels, and tooth powders. Components of such toothpaste, and tooth gels generally include one or more of a dental abrasive, generally in an amount of from about 10% to 50% by weight based on the total weight of the oral care composition, a surfactant in an amount of from about 0.5% to 10% by weight, a thickening agent in an amount of from about 0.1% to 5% by weight, a humectant in an amount of from about 10% to 55% by weight, a flavoring agent in an amount of from about 0.04% to 2% by weight, a sweetening agent in an amount of from about 0.1% to 3% by weight, a coloring agent in an amount of from 0.01% to 0.5% by weight, and water in an amount of from about 2% to 45% by weight. Such toothpastes or tooth gels may also include one or more of an anticaries agent in an amount of from about 0.05% to 0.3% by weight (e.g., fluoride ion), and an anticalculus agent in an amount of from about 0.1% to 13% by weight. Tooth powders, of course, contain substantially all non-liquid components.

Other preferred compositions of the present invention are in the form of microcaps or more commonly known as gel beads, which generally comprise a flavorant in an amount of from about 0.1% to 10% by weight based on the total weight of the oral care composition, a lipophilic filler in an amount of from about 1% to 60% by weight, an emulsifier in an amount of from about 0.1% to 5% by weight and a sweetening agent in an amount of from about 0.01% to 3% by weight.

Chewing gum compositions typically include one or more of gum base in an amount of from about 50% to 99% by weight based on the total weight of the oral care composition, a flavoring agent in an amount of from about 0.4% to 2% by weight and a sweetening agent in an amount of from about 0.01% to 5% by weight.

The term "lozenge" as used herein includes: breath mints, troches, pastilles, microcapsules, and fast-dissolving solid forms including freeze dried forms (cakes, wafers, thin films, and tablets) and fast dissolving solid forms including compressed tablets. The term "fast dissolving solid form" as used herein means that the solid dosage form dissolves in less than about 60 seconds, preferably less than about 15 seconds, more preferably less than about 5 seconds, after placing the solid dosage form in the oral cavity. Lozenges include discoid shaped solids comprising a therapeutic agent in a flavored base. The base may be a hard sugar candy, glycerinated gelatin, or combination of sugar with sufficient mucilage to give it form. Lozenge compositions (compressed tablet type) typically include one or more fillers (compressible sugar), flavoring agents and lubricants.

The term "oral care effective amount" as used herein is meant to be an amount of at least one tropolone compound of the present invention, sufficient to prevent or treat the diseases or conditions of the oral cavity, or to significantly eliminate or at least suppress the presence of undesirable microorganisms in the oral cavity, without causing side effects within the scope of sound medical and dental judgment. The oral care effective amount of the tropolone compounds of the present invention may vary with the particular condition (e.g., to treat disease of the oral cavity or malodor) being treated, the age and physical condition of the patient being treated, the severity of the condition, the duration of treatment, the nature of concurrent therapy, the specific form (i.e., salt) of the tropolone compound of the present invention employed, and the particular carrier from which the tropolone compound of the present invention is applied.

The concentration of the tropolone compounds in the oral care composition of the present invention depends on the type of composition (e.g., toothpaste, mouthwash and rinse, lozenge, gum, etc.) used to apply the tropolone compounds of the present invention to the gingival/mucosal tissue and/or teeth, due to differences in efficiency of the compositions contacting the tissue and teeth and due also to the amount of the composition generally used. The concentration may also depend on the diseases or conditions being treated.

In a preferred embodiment, the oral care compositions of the present invention may comprise at one least one tropolone compound of the present invention in amounts of from about 0.001% to 10.0% by weight based on the total weight of the oral care composition, preferably from about 0.01% to 5.0% by weight, and more preferably from about 0.01% to 2.0% by weight with the remainder of the formulation being the carrier and other materials known in the art as oral care composition components. Such additional components may include buffers, surfactants, solubilizers, preservatives, emulsifying agents, isotonizers, stabilizers, pH adjusting agents, sweeteners, coloring agents, and the like.

In another embodiment of the present invention, there is provided a method of treating or preventing diseases or conditions of the oral cavity in warm-blooded animals including humans, by applying an oral care effective amount of the oral care composition of the present invention to the oral cavity. The oral care effective amount of the oral care compositions of the present invention is preferably applied to the mucosal tissue of the oral cavity, to the gingival tissue of the oral cavity, and/or surface of the teeth, for the treatment or prevention of the above-mentioned diseases or conditions of the oral cavity, in one or more conventional ways. For example, the gingival or mucosal tissue may be rinsed with a solution (e.g., mouthwash, rinse) containing the tropolone compounds of the present invention; if the tropolone compounds are included in a dentifrice (e.g., toothpaste, tooth gel, or tooth powder), the gingival/mucosal tissue or teeth may be bathed in the liquid and/or lather generated by brushing the teeth; etc., for a sufficient time, preferably from about 10 seconds to 10 minutes, more preferably from about 30 seconds to 60 seconds.

The method of the present invention generally further involves expectoration of most of the composition following such contact. The frequency of such contact is preferably from about once a week to about four times per day, more preferably from about 3 times per week to three times per day, even more preferably once per day to twice per day. The period of such treatment typically ranges from about one day to a lifetime. For particular diseases or conditions of the oral cavity the duration of treatment depends on the severity of the oral disease or condition being treated, the particular delivery form utilized and the patient's response to treatment. If the delivery to the periodontal pockets is desirable, such as with the treatment of periodontal disease, a mouthwash or rinse can be delivered to the periodontal pocket using a syringe or a water injection device, for example. After irrigating, the subject can swish the wash in the mouth to also cover the dorsal portion of the tongue and other gingival/mucosal surfaces. In addition to toothpaste, non-abrasive gel, tooth gel, etc., can be brushed onto the tongue surface and other gingival and mucosal tissues of the oral cavity.

Other non-limiting examples include chewing gum that contains tropolone compounds of the present invention, chewing or sucking on a breath tablet or lozenge. Preferred methods of applying the oral care compositions of the present invention to the gingival/mucosal tissue and/or teeth include rinsing with a mouthwash or rinse solution and brushing with a dentifrice. Other methods of topically applying tropolone compounds of the present invention to the gingival/mucosal tissue and surfaces of the teeth are apparent to those skilled in the art.

The present substituted tropolone compounds of Formula (I) employed in the present invention may be prepared from readily available starting materials using the following general methods and procedures. It will be understood that where typical or preferred process conditions (i.e. reaction temperatures, times, mole ratios of reactants, solvents, pressures, etc.) are given, other process conditions may also be used unless otherwise stated. Optimum reaction conditions may vary with the particular reactants or solvents used, however such reaction conditions may be determined by one of ordinary skill in the art through routine optimization procedures.

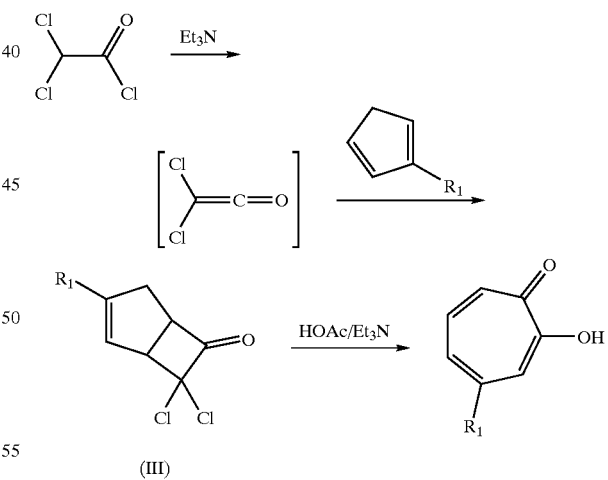

Scheme 1

Compounds of Formula (I) can be prepared as shown in Scheme 1 by reacting dichloroacetyl chloride with an $R_1$-substituted cyclopentadiene compound in the presence of a base such as triethylamine to yield a cycloadduct of Formula (III). The cycloadduct of Formula (III) is then treated with an acid such as acetic acid and a base such as triethylamine to yield the final desired product, a 4-alkyltropolone compound. When $R_1$ is isopropyl the resulting compound is hinokitiol which is used as a starting material in Scheme 2.

Scheme 2

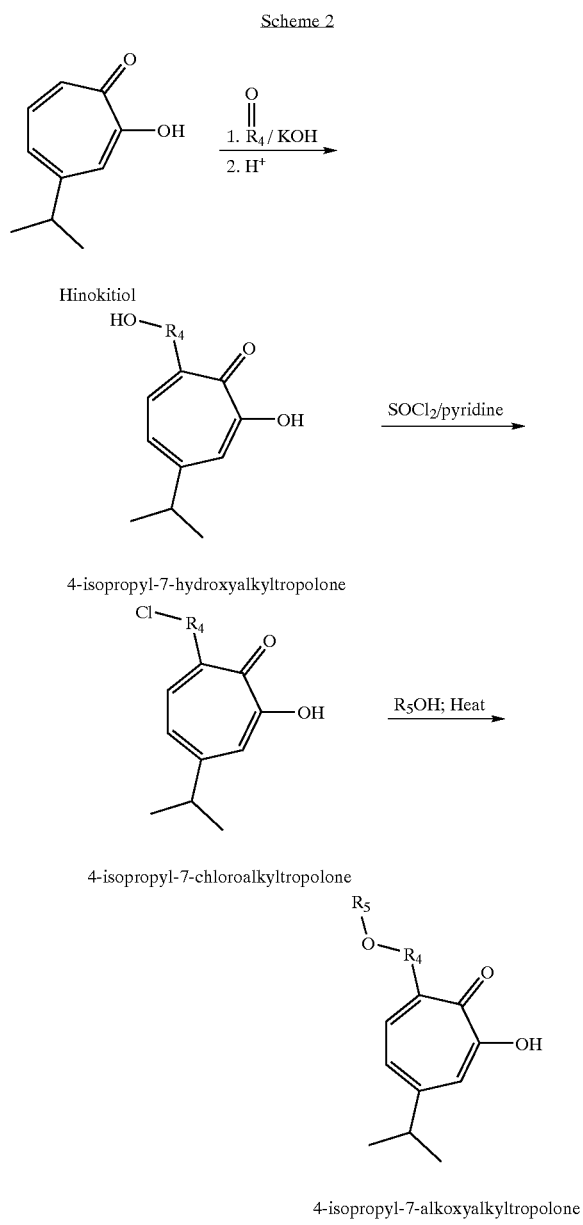

4-isopropyl-7-alkoxyalkyltropolone

Scheme 3

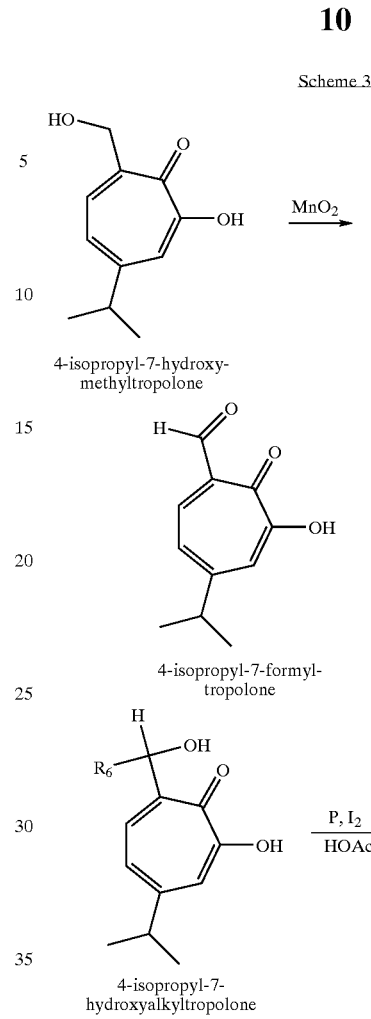

Compounds of Formula (I) can further be prepared as shown in Scheme 2 by treating hinokitiol with a carbonyl compound ($R_4$=O, wherein $R_4$ is an alkyl group) such as formaldehyde, acetaldehyde, proprionaldehyde, butyraldehyde, and the like, in the presence of a base such as potassium hydroxide, and thereafter adding an acid such as hydrochloric acid to yield a 4-isopropyl-7-hydroxyalkyltropolone compound. The 4-isopropyl-7-hydroxyalkyltropolone compound is then treated with a chlorinating agent such as $SOCl_2$ in the presence of a base such as pyridine to yield a 4-isopropyl-7-chloroalkyltropolone compound. The 4-isopropyl-7-chloroalkyltropolone is reacted with an alcohol ($R_5OH$; wherein $R_5$ is an alkyl group) such as methanol, ethanol, propanol, and the like, in the presence of heat to yield the corresponding a 4-isopropyl-7-alkoxyalkyltropolone compound.

Compounds of Formula (I), can further be prepared as shown in Scheme 3 by reacting 4-isopropyl-7-hydroxymethyltropolone with an oxidizing agent such as $MnO_2$ to yield 4-isopropyl-7-formyltropolone. The starting compound, 4-isopropyl-7-hydroxymethyltropolone, may be prepared by reacting hinokitiol with formaldehyde in the presence of a base such as potassium hydroxide, and thereafter treating the reaction with an acid such as hydrochloric acid. 4-isopropyl-7-formyltropolone is reacted with an alkylmagnesium bromide compound ($R_6MgBr$; wherein $R_6$ is an alkyl group) and the reaction is quenched with an acid such as hydrochloric acid to yield a 4-isopropyl-7-hydroxyalkyltropolone compound. The 4-isopropyl-7-hydroxyalkyltropolone compound is treated with a reducing agent such as phosphorus, preferably red phosphorus, in the presence of an acid such as acetic acid, whereupon as oxidizing agent such as iodine is added to the reaction to yield a final product of a 4-isopropyl-7-alkyltropolone compound.

The following examples are offered only to illustrate the invention, and should not be interpreted as a limitation thereon. For example, optimum reaction conditions may vary with the particular reactants or solvents used, however such reaction conditions may be determined by one of ordinary skill in the art through routine optimization procedures.

EXAMPLE 1

Synthesis of 4-Methyltropolone

Scheme A

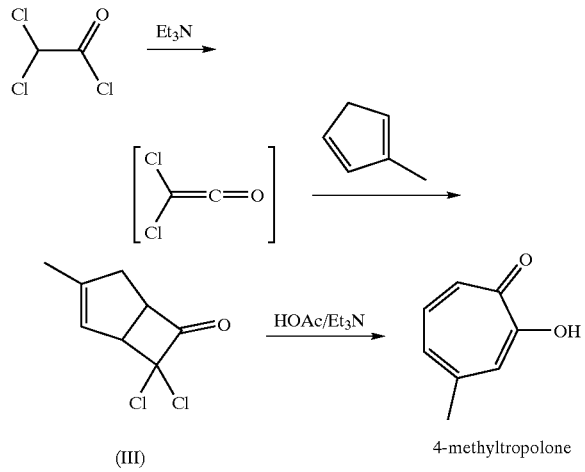

As illustrated in Scheme A, a solution comprising 25 mL of triethylamine and 100 mL of a mixture of hexanes was added dropwise to a solution containing 48.5 g of methylcyclopentadiene (prepared from cracking methylcyclopentadiene dimer) and 22.5 g of dichloroacetyl chloride in 200 mL of a mixture of hexanes at 0° C. The mixture was stirred for about one hour and thereafter poured into 150 mL of water at about 0° C. The layers were separated and the aqueous phase was extracted with two 75 mL portions of hexanes. The combined organic layers were washed twice with water, then dried over $Na_2SO_4$ and concentrated to yield an oil. Fractional distillation was performed under vacuum to yield a cycloadduct of Formula (III), which was dissolved in 80 mL of acetone. The resulting solution was then added to a solution containing 28.5 mL of acetic acid, 82.5 mL of triethylamine, 36 mL of water and 100 mL of acetone. The mixture was refluxed under nitrogen for about four hours. The acetone was removed from the mixture under reduced pressure. An additional 100 mL of water was added and then the solution was extracted three times each with 100 mL portions of ether. The combined organic extracts were washed with water and dried over $MgSO_4$. The final product, 4-methyltropolone, was recrystallized from hexanes to yield a white solid.

EXAMPLE 2

Synthesis of 4-Isopropyl-7-methoxymethyltropolone

Scheme B

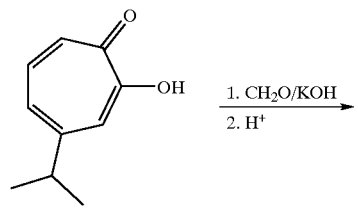

Hinokitiol

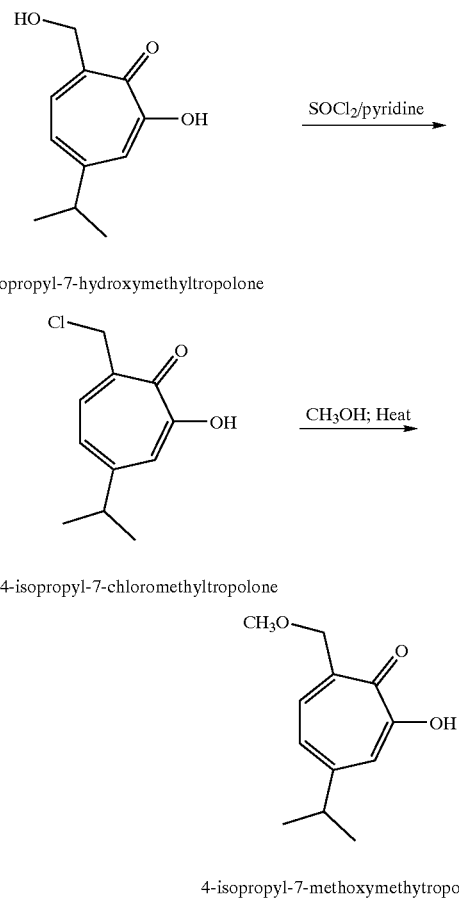

As illustrated in Scheme B, a solution comprising 10 g of hinokitiol and 18.8 mL of 25% aqueous KOH was heated to 60° C. under argon. Formaldehyde was added in 1 mL portions every 30 minutes until a total of 10 mL was added. The reaction mixture was concentrated to a yellow paste and 300 mL of acetone was added. The resulting yellow solid was collected and washed with acetone. The solid was suspended in 250 mL in dichloromethane and 50 mL of 2.0M HCl was added. The aqueous layer was washed with dichloromethane and the combined organic layers were washed with water, and then dried over $Na_2SO_4$. The solvent was removed under vacuum leaving an oil which solidified upon trituration with petroleum ether. An ice cold solution of 4.0 g of 4-isopropyl-7-hydroxymethyltropolone and 1.8 mL of pyridine in 100 mL of diethyl ether was vigorously stirred for two hours as a solution of $SOCl_2$ (2.5 mL) in 80 mL of ether was added thereto. The resulting mixture was concentrated to yield a solid. Boiling petroleum ether was added to the solid. The resulting mixture was filtered and the filtrate was cooled to yield 4-isopropyl-7-chloromethyltropolone in the form of a solid. The solid product was then refluxed in methanol under nitrogen for about two hours and then concentrated to yield a golden oil. A stream of $N_2$ gas was passed over the oil until it solidified to yield 4-isopropyl-7-methoxymethyltropolone in the form of a pale yellow solid.

EXAMPLE 3

Synthesis of 4-Isopropyl-7-hexyltropolone

Scheme C

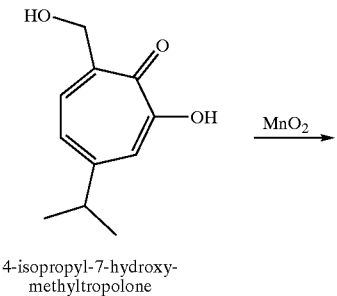

4-isopropyl-7-hydroxy-
methyltropolone

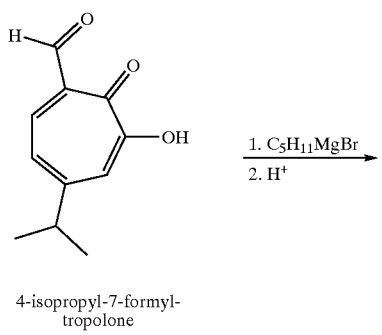

4-isopropyl-7-formyl-
tropolone

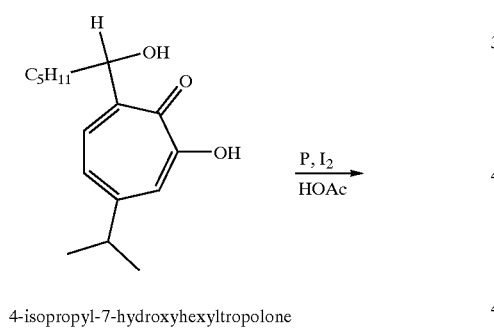

4-isopropyl-7-hydroxyhexyltropolone

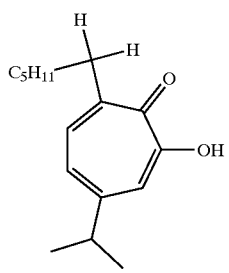

4-isopropyl-7-hexyltropolone

As illustrated in Scheme C, 4-isopropyl-7-methoxymethyltropolone as produced in Example 2 was oxidized in the presence of MnO₂ to yield 0.85 g of 4-isopropyl-7-formyltropolone. 4-isopropyl-7-formyltropolone was added to ether to yield a solution, which was stirred under $N_2$ at 0° C. 5 mL of a 2.0 M solution of pentylmagnesium bromide was added to the solution via a syringe. The mixture was stirred for about 45 minutes and then quenched with 20 mL of water. 10 mL of 0.5 M HCl and 100 mL of ether was added to the mixture. The layers were separated and the organic layer was dried over $Na_2SO_4$. The solvent was removed and the resulting oil was triturated with petroleum ether to yield 4-isopropyl-7-hydroxyhexyltropolone in the form of a yellow oil. The oil product was mixed in 2 mL of water, 1 g of red phosphorus and 15 mL of acetic acid. The mixture was stirred well and 1 g of $I_2$ was added. The reaction mixture was refluxed for about an hour, and thereafter filtered. 150 mL of water was added the filtrate. $K_2CO_3$ was added to the mixture to generate a basic pH. The mixture was extracted with petroleum ether. The organic layer was washed with $Na_2S_2O_3$ and then with water, and was dried over $Na_2SO_4$ to yield 4-isopropyl-7-hexyltropolone in the form of an oil.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A compound of Formula (I), isomers and pharmaceutically acceptable salts thereof,

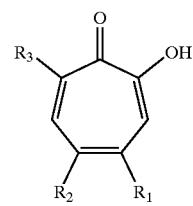

I wherein $R_1$ is an alkyl group having 1 to 6 carbon atoms, $R_2$ is hydrogen, and $R_3$ is an alkoxyalkyl group.

2. The compound of claim 1 wherein the alkoxyalkyl group is selected from the group consisting of methoxymethyl and hexloxymethyl.

3. The compound of claim 2 wherein $R_1$ is selected from the group consisting of methyl and isopropyl.

4. The compound of claim 3 wherein $R_1$ is isopropyl and $R_3$ is hexloxymethyl.

5. The compound of claim 2 wherein the alkoxyalkyl is methoxymethyl.

6. A compound of Formula (I), isomers and pharmaceutically acceptable salts thereof,

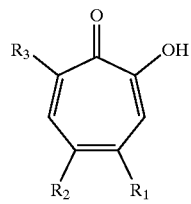
wherein $R_1$ is methyl, $R_2$ is hydrogen, and $R_3$ is hydroxymethyl.
7. A compound of Formula (I), isomers and pharmaceutically acceptable salts thereof,
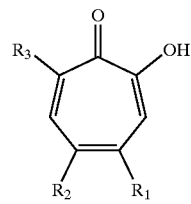
wherein $R_1$ is isopropyl, $R_2$ is hydrogen, and $R_3$ is an alkyl group having 1 to 6 carbons.
8. The compound of claim 7 wherein $R_3$ is hexyl.
* * * * *